(12) United States Patent
Sweeney et al.

(10) Patent No.: US 8,017,161 B2
(45) Date of Patent: Sep. 13, 2011

(54) BOWMAN-BIRK INHIBITOR COMPOSITIONS FOR TREATMENT OF MUSCULAR ATROPHY AND DEGENERATIVE MUSCLE DISEASE

(75) Inventors: H. Lee Sweeney, Philadelphia, PA (US); Carl A. Morris, Quincy, MA (US); Ann R. Kennedy, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 822 days.

(21) Appl. No.: 10/566,796

(22) PCT Filed: Jul. 30, 2004

(86) PCT No.: PCT/US2004/024718
§ 371 (c)(1),
(2), (4) Date: Apr. 2, 2008

(87) PCT Pub. No.: WO2005/011596
PCT Pub. Date: Feb. 10, 2005

(65) Prior Publication Data
US 2008/0300179 A1     Dec. 4, 2008

Related U.S. Application Data

(60) Provisional application No. 60/491,695, filed on Aug. 1, 2003.

(51) Int. Cl.
*A01N 65/00* (2009.01)
(52) U.S. Cl. .................................... 424/725
(58) Field of Classification Search .................. None
See application file for complete search history.

(56) References Cited

U.S. PATENT DOCUMENTS

| | | | | |
|---|---|---|---|---|
| 2,596,090 A | * | 5/1952 | Baxter | 549/412 |
| 2,891,864 A | * | 6/1959 | Baxter | 426/72 |
| 5,217,717 A | | 6/1993 | Kennedy et al. | 424/195.1 |
| 5,961,980 A | * | 10/1999 | Kennedy et al. | 424/757 |

FOREIGN PATENT DOCUMENTS

| | | |
|---|---|---|
| CA | 1219764 | 3/1987 |
| WO | WO 97/25961 | 7/1997 |
| WO | WO 00/53232 | 9/2000 |

OTHER PUBLICATIONS

Hove et al., Journal of Nutrition, Jan. 1947, 33 (1), 95-106.*
Lynch, Exp. Opin. Ther. Patents, 2001, 11 (4), pp. 587-601.*
Allen et al., "Apoptosis: a mechanism contributing to remodeling of skeletal muscle in response to hindlimb unweighting", Am. J. Physiol. 1997 273 (Cell Physiol. 42): C579-0587.
Allen et al., "Myonuclear Domains in Muscle Adaptation and Disease", 1999 Muscle Nerve 22: 1350-1360.
Badalamente et al., "Delay of Muscle Degeneration and Necrosis in mdx Mice by Calpain Inhibition", 2000 Muscle Nerve 23: 106-111.
Barton-Davis et al., "Viral Mediated Expression of Insulin-Like Growth Factor I Blocks the Aging-Related Loss of Skeletal Muscle Function", Proc. Natl Acad Sci USA vol. 95, No. 26. Dec. 22, 1998, pp. 15603-1560.
Billings et al., "Distribution of the Bowman Birk protease inhibitor in mice following oral administration", 1992, Cancer Letters 62 191-197.
Birk et al., "The Bowman-Birk inhibitor", Int. J. Peptide Protein Res. 25, 1985, 113-13.
Bodine et al., "Akt/mTOR pathway is a crucial regulator of skeletal muscle hypertrophy and can prevent muscle atrophy in vivo", Nature Cell Biology, vol. 3, Nov. 2001, pp. 1014-1019.
Buetler et al., "Green Tea Extract Decreases Muscle Necrosis in mdx Mice and Protects Against Reactive Oxygen Species", Am. J. Clin. Nutr. 2002; 75:749-53.
Criswell et al., "Overexpression of IGF-I in skeletal muscle of transgenic mice does not prevent unloading-induced atrophy", Am. J. Physiol. 1998 275: E373-E379.
Goldberg et al., "Protein Turnover in Skeletal Muscle", The Journal of Biological Chemistry, vol. 244, No. 12, 1969 pp. 3223-3229.
Gordon et al., "Plasticity in Skeletal, Cardiac, and Smooth Muscle Selected Contribution: Skeletal muscle focal adhesion kinase, paxillin, and serum response factor are loading dependent", J Appl Physiol 2001 90: 1174-1183.
Granchelli et al., "Cromolyn Increases Strength in Exercised MDX Mice", Research Communications in Molecular Pathology and Pharmacology, vol. 91, No. 3 Mar. 1996 pp. 287-296.
Hornberger et al., "Regulation of translation factors during hindlimb unloading and denervation of skeletal muscle in rats", Am. J. Physiol. 2001 281:C179-C187.
Hunter et al., "Activation of an alternative NF-kB pathway in skeletal muscle during disuse atrophy", The FASEB Journal, 2002 vol. 16 pp. 529-538.
Ikemoto et al., "Space shuttle flight (STS-90) enhances degradation of rat myosin heavy chain in association with activation of ubiquitin-proteasome pathway", The FASEB Journal published online Mar. 12, 2001.
Jaspers et al., "Atrophy and growth failure of rat hindlimb muscles in tail-cast suspension", The American Physiological Society, 1984 pp. 1472-1479.
Kennedy et al., "Preparation and Production of a Cancer Chemopreventative Agent, Bowman-Birk Inhibitor Concentrate", Nutr Cancer 1993 vol. 19, No. 3, pp. 281-302.
Ann R. Kennedy, "Anticarcinogenic Activity of Protease Inhibitors", Protease Inhibitors as Cancer Chemopreventive Agents, edited by Walter Troll and Ann R. Kennedy. Plenum Press, New York, 1993.
Ann R. Kennedy, "Chemopreventative Agents: Protease Inhibitors", Pharmacol. Ther. vol. 78, No. 3, pp. 167-209, 1998.
Larionova et al., "Inhibition of Cathepsin G and Human Granulocyte Elastase by Multiple Forms of Soybean Inhibitor of Bowman-Birk Type", Biokhimiya 1993 58:1437-1444.

(Continued)

*Primary Examiner* — Michael Meller
(74) *Attorney, Agent, or Firm* — Licata & Tyrrell P.C.

(57) ABSTRACT

Methods for use of a composition comprising Bowman-Birk Inhibitor (BBI) or a derivative thereof in the treatment and/or prevention of skeletal muscle atrophy, to improve of skeletal muscle function, and to alleviate symptoms and/or slow progression of degenerative skeletal muscle diseases or disorders are provided.

17 Claims, No Drawings

OTHER PUBLICATIONS

Loughna et al., "Effect of Inactivity and Passive Stretch on Protein Turnover in Phasic and Postural Rat Muscles", J. Appl. Physiol. 1986 61(1) 173-179.

Mitchell et al., "A muscle Precursor Cell-Dependent Pathway Contributes to Muscle Growth After Atrophy", Am J Physiol Cell Physiol 281: C1706-C1715, 2001.

Nikawa et al., "Effects of a Soy Protein Diet on Exercise-Induced Muscle Protein Catabolism in Rats", Nutrition 18:490-495, 2002.

Oreffo et al., "Actue effects of the Bowman-Birk protease inhibitor in mice", Toxicology, 69 (1991) 165-176.

Sangorrin et al., "Myofibril-bound Serine Protease and its Endogenous Inhibitor in Mouse: Extraction, Partial Characterization and Effect on Myofibrils", Comparative Biochemistry and Physiology Part B 131 (2002) 713-723.

Sawada et al., "Therapeutic Effect of Camostat Mesilate on Duchenne Muscular Dystrophy in mdx Mice", Pharmaceutical Society of Japan, 2003, Biol. Pharm. Bull. 26(7) 1025-1027.

Solomon et al., "Importance of the ATP-Ubiquitin-Proteasome Pathway in the Degradation of Soluble and Myofibrillar Proteins in Rabbit Muscle Extracts", The Journal of Biological Chemistry, 1996, vol. 271, No. 43, 26690-26697.

Spencer et al., "Overexpression of Calpastatin Transgene in mdx Muscle Reduces Dystrophic Pathology", Human Molecular Genetics, 2002, vol. 11, No. 21, pp. 2645-2655.

Stevenson et al., "Global Analysis of Gene Expression Patterns During Disuse Atrophy in Rat Skeletal Muscle", J. Physiol. 2003;551;33-48.

Tada et al., "Effect of Different Dietary Protein Composition on Skeletal Muscle Atrophy by Suspension Hypokinisia/Hypodynamia in Rats", J. Nutr. Sci. Vitaminol. 48. 115-119, 2002.

Taillandier et al., "Coordinate Activation of Lysosomal, Ca2+-Activated and ATP-ubiquitin-dependent Proteinases in the Unweighted Rat Soleus Muscle", Biochem. J. (1996) 316, 65-72.

Tawa et al., "Inhibitors of the Proteasome Reduce the Accelerated Proteolysis in Atrophying Rat Skeletal Muscles", J. Clin. Invest., vol. 100, No. 1, pp. 197-203, 1997.

Tidball et al., "Expression of a Calpastatin Transgene Slows Muscle Wasting and Obviates Changes in Myosin Isoform Expression During Murine Muscle Disuse", J. Physiol. 2002;545;819-828.

Tischler et al., "Different Mechanisms of Increased Proteolysis in Atrophy Induced by Denervation or Unweighting of Rat Soleus Muscle", Metabolism, vol. 39, No. 7, 1990: pp. 756-763.

Ware et al., "Soybean Bowman-Birk Protease Inhibitor Is a Highly Effective Inhibitor of Human Mast Cell Chymase", Archives of Biochemistry and Biophysics, vol. 344, No. 1, pp. 133-138, 1997.

Yavelow et al., "Nanomolar Concentrations of Bowman-Birk Soybean Protease Inhibitor Suppress x-ray-induced Transformation in Vitro", Proc. Natl. Acad. Sci. USA, vol. 82, pp. 5395-5399, 1985.

Hoffman et al., "Molecular pathophysiology and targeted therapeutics for muscular dystrophy", TRENDS in Pharmalogical Sciences 2001 22(9):465-470.

Medline Accession No. NLM1450492, Satoyoshi et al., "Therapeutic trials on progressive muscular dystrophy", Jul. 1992 31(7):841-846-Abstract.

Medline Biosis Abstract No. PREV200300401641, Morris et al., "Dietary intake of a soy-derived protease inhibitor attenuates the skeletal muscle mass loss associated with disuse atrophy in mice", Mar. 2003—Abstract.

Medline Accession No. NLM3711932, Tsuji et al., "Successful treatment of murine muscular dystrophy with the protease inhibitor bestatin", Feb. 1986 72(2-3):183-194—Abstract.

Supplementary Search Report from EPO application No. 04779693.3, Dec. 6, 2007, EPO.

Official Communication from EPO application No. 04779693.3, Mar. 4, 2008, EPO.

Official Communication from EPO application No. 04779693.3, Feb. 8, 2010, EPO.

Hoffman E.P. and Dressman, P., "Molecular Pathophysiology and Targeted Therapeutics for Muscular Dystrophy", TRENDS in Pharmacological Sciences 2001 22(9):465-470.

Satoyoshi, E., "Therapeutic Trials on Progressive Muscular Dystrophy", Internal Medicine Jul. 1992 31(7):841-846 with Abstract from Medline Accession No. NLM1450492.

Medline Biosis Abstract No. PREV200300401641, Morris et al., "Dietary Intake of a Soy-derived Protease Inhibitor Attenuates the Skeletal Muscle Mass Loss Associated with Disuse Atrophy in Mice", Mar. 2003.

Tsuji S. and Matsushita, H. "Successful Treatment of Murine Muscular Dystrophy with the Protease Inhibitor Bestatin", Journal of the Neurological Sciences Feb. 1986 72(2-3):183-194 with Abstract from Medline Accession No. NLM3711932.

Connolly et al., "Three Mouse Models of Muscular Dystrophy: the Natural History of Strength and Fatigue in Dystrophin-, Dystrophin/Utrophin-, and Laminin ∝2-Deficient Mice," Neuromuscular Disorders 2001 11:703-711.

Hayashi et al. "Studies on Degradation of Myofibrillar Proteins by Mast Cell Serine Protease" Shikoku Acta Medica 1983 39(6):580-590 (English summary provided).

Katunuma et al. "Abnormal Expression of a Serine Protease in Human Dystrophic Muscle" Journal of Biochemistry 1978 83(2):625-628.

Sanada et al. "Serine Protease in Mice with Hereditary Muscular Dystrophy" Journal of Biochemistry 1978 83(1):27-33.

\* cited by examiner

BOWMAN-BIRK INHIBITOR COMPOSITIONS FOR TREATMENT OF MUSCULAR ATROPHY AND DEGENERATIVE MUSCLE DISEASE

This patent application claims the benefit of priority from U.S. Provisional Patent Application Ser. No. 60/491,695, filed Aug. 1, 2003, herein incorporated by reference in its entirety.

FIELD OF THE INVENTION

The present invention provides methods for use of compositions comprising Bowman-Birk Inhibitor (BBI) or a derivative thereof in the treatment and/or prevention of skeletal muscle atrophy and degenerative skeletal muscle diseases. For example, compositions comprising BBI or a derivative thereof can be administered to a subject to prevent or treat disuse atrophy during periods of bed rest/inactivity or to prevent muscle atrophy during spaceflight. Further, the functional improvement of skeletal muscle upon treatment with a composition comprising BBI or a derivative thereof is indicative of such compositions being useful in alleviating symptoms and/or slowing the progression of degenerative skeletal muscle diseases including, but in no way limited to, muscular dystrophy, amyotrophic lateral sclerosis, spinal muscle atrophy and spinal cord injury.

BACKGROUND OF THE INVENTION

Skeletal muscle atrophy, the loss of muscle mass, is associated with removal of load-induced signaling either during disuse or under microgravity conditions. This atrophy is mediated by slowing/inhibition of growth signaling pathways and an increase in pathways associated with protein degradation (Goldberg, A. L. J Biol Chem 1969 244: 3223-3229; Jaspers, S. R. and Tischler, M. E. J Appl Physiol 1984 57: 1472-1479; Loughna et al. J Appl Physiol 1986 61: 173-179). This rapid loss of muscle mass and strength, especially in an aging population, represents a significant health problem.

As the primary response to the removal of load appears to be changes in either protein synthesis or degradation, a possible treatment strategy to decrease muscle atrophy would be to restore normal signaling for either or both of these processes. Investigation of growth pathway signaling has showed significant changes in the levels and activities of key signaling proteins following unloading (Gordon et al. J Appl Physiol 2001 90: 1174-1183; Hornberger et al. 2001 Am J Physiol Cell Physiol 281: C179-187; Hunter et al. 2002 Faseb J 16: 529-538; Mitchell, P. O. and Pavlath, G. K. Am J Physiol Cell Physiol 2001 281: C1706-1715). Overexpression of a constitutively active signaling protein, Akt, generated significant muscle hypertrophy and inhibited muscle atrophy associated with denervation (Bodine et al. Nat Cell Biol 2001 3: 1014-1019). However, upregulation of IGF-I, a potent activator of muscle hypertrophy (Barton-Davis et al. Proc Natl Acad Sci USA 1998 95: 15603-15607) did not inhibit the loss in muscle mass associated with hindlimb suspension (Criswell et al. Am J Physiol 1998 275: E373-379). This is indicative of unknown mechanisms blocking the IGF-I initiated cascade of growth pathways during disuse.

Rather than targeting the growth pathways, another potential therapeutic method to counter disuse atrophy would be to prevent increased activation of protein degradation. The loss of muscle protein, most notably myofibrillar protein degradation, is thought to occur primarily through activation of the ubiquitin-proteasome pathway (Taillandier et al. Biochem J 1996 316: 65-72; Tawa et al. J Clin Invest 1997 100: 197-203; Ikemoto et al. Faseb J 2001 15: 1279-1281) and causes declines in the force generating capacity of the muscle. However, two other proteolytic pathways, the $Ca^{2+}$-dependent pathway (via calpains) and lysosomal pathway (via cathepsins B+L), have been associated with muscle atrophy and implicated in the initial proteolysis of the myofibrillar proteins (Tidball, J. G. and Spencer, M. J. J Physiol (Lond) 2002 545: 819-828; Tischler et al. Metabolism 1990 39: 756-763), though the role of these pathways in the loss of muscle protein is still unclear (Ikemoto et al. Faseb J 2001 15: 1279-1281). However, rats fed a 20% soy protein isolate diet were reported to have significantly higher calpastatin activity in gastrocnemius muscle than rats fed a casein diet (Nikawa et al. Nutrition 2002 18: 490-495, 2002). Thus, soy protein diets are suggested to prevent exercise induced protein degradation in skeletal muscle, possible inhibiting the calpain-mediated proteolysis (Nikawa et al. Nutrition 2002 18: 490-495, 2002). Studies investigating the effect of soy protein isolated on muscle atrophy caused by suspension hypokinesia have also been suggested to indicate that soy protein isolate causes a reduction in proteolysis of myofibrillar protein in skeletal muscles through reduction of calpain and proteosome activities, in consequence to ameliorate muscle atrophy (Tada, O. and Yokogoshi, H. J Nutritional Science Vitaminology (Tokyo) 48: 115-119, 2002).

Alternatively, recent work has suggested serine protease cascades may provide a mechanism for the initiation of protein degradation leading to muscle atrophy (Sangorrin et al. Comp Biochem Physiol B Biochem Mol Biol 2002 131: 713-723; Stevenson et al. J Physiol (Lond): 2003 2003.044701).

To date, however, there are no known oral pharmacological treatments for disuse atrophy and electrical stimulation to maintain muscle tone is still the primary method used to inhibit muscle loss during extended periods of inactivity.

Duchenne muscular dystrophy (DMD) is a degenerative disease that leads to progressive muscle weakness and atrophy. The disease results from the mutations in the gene encoding the cytoskeletal protein dystrophin. Dystrophin associates with a large complex of membrane-bound proteins, together the dystrophin glycoprotein complex (DGC), which is considered necessary for normal muscle cell membrane stability. The loss of dystrophin, and the associated DGC, results in compromised structural integrity of the muscle plasma membrane producing damaging cycles of muscle necrosis and regeneration.

To prevent DMD, it will likely be necessary to therapeutically replace either dystrophin itself or another protein capable of restoring appropriate function to the muscle. However, other therapies may greatly improve quality of life and diminish the severity of the disease, while the difficulties of protein replacement are overcome.

The loss of membrane integrity of muscles in patients with DMD is suggested to result in an increased influx of extracellular calcium, leading to activation of protein degradation pathways and stimulation of inflammatory processes. Thus, various attempts have been made to decrease the activation of the protein degradation pathway and/or inhibit stimulation of the inflammatory response.

For example, a correlation has been shown between calcium-dependent protease or calpain activity and dystrophic muscle and muscle necrosis. Overexpression of the transgene of calpastatin, a specific endogenous inhibitor of calpains was shown to reduce dystrophic pathology in mdx mice, a murine model for Duchenne muscular dystrophy (Spencer, M. J. and Mellgren, R. L. Human Molecular Genetics 2002 11(21):

2645-55). Administration of the calpain inhibitor leupeptin has also been correlated with retention of myofiber size in the mdx murine model. (Badalamente, M. A. and Stracher, A. Muscle & Nerve 2000 23(1):106-11).

A trypsin-like protease designated as dystrypsin has also been reported to be markedly activated in the muscle microsomal fraction immediately before the onset of clinical signs in mdx mice. Camostat mesilate, a low-molecular weight inhibitor of trypsin-like proteases, including dystrypsin, has been suggested as a candidate drug for Duchenne muscular dystrophy (Sawada et al. Biological & Pharmaceutical Bulletin 2003 26(7):1025-7).

Direct injections of a mast cell stabilizer, cromolyn, have also been shown to increase strength in exercised mdx mice (Granchelli et al., Res. Commun. in Mol. Pathol. and Pharm. 1996 91(3): 287-96).

In addition, dietary supplementation with green tea extract, an antioxidant, was disclosed to reduce necrosis and decrease oxidative stress in mdx mice and cultured mouse C2C12 myotubes, respectively. (Buetler et al. American J. of Clin. Nutrition 2002 75(4): 749-53).

Currently, the only established treatment for muscular dystrophy, however, is the use of steroids such as prednisone and deflazacourt. These treatments slow the loss of muscle only slightly and produce significant side effects.

SUMMARY OF THE INVENTION

An object of the present invention is to provide a method for treatment or prevention of skeletal muscle atrophy in a subject which comprises administering to the subject a composition comprising Bowman-Birk Inhibitor or a derivative thereof.

Another object of the present invention is to a method for improving skeletal muscle function in a subject which comprises administering to the subject a composition comprising Bowman-Birk Inhibitor or a derivative thereof.

Another object of the present invention is to provide a method for treating or preventing skeletal muscle degeneration in a subject which comprises administering to the subject a composition comprising Bowman-Birk Inhibitor or a derivative thereof.

Yet another object of the present invention is to provide a method for alleviating symptoms or slowing disease progression in a subject suffering from a degenerative skeletal muscle disorder or disease, including but in no way limited to, muscular dystrophy, amyotrophic lateral sclerosis, spinal muscle atrophy and spinal cord injury, which comprises administering to the subject a composition comprising Bowman-Birk Inhibitor or a derivative thereof.

DETAILED DESCRIPTION OF THE INVENTION

Though progress identifying key elements associated with skeletal muscle changes in growth signaling (Bodine et al. Nat Cell Biol 2001 3: 1014-1019; Hunter et al. Faseb J 2002 16: 529-538; Mitchell, P.O. and Pavlath, G. K. Am J Physiol Cell Physiol 2001 281: C1706-1715), apoptosis (Allen et al. Am J Physiol 1997 273:C579-587; Allen et al. Muscle Nerve 1999 22:1350-1360), and protein degradation (Taillandier et al. Biochem J 1996 316: 65-72; Solomon, V, and Goldberg, A. L. J Biol Chem 1996 271: 26690-26697; Ikemoto et al. Faseb J 2001 15:1279-1281) has been achieved, there has been limited success in attenuating the overall response to atrophy, namely loss of muscle mass and strength. Dissection of these pathways has not completely defined all the required elements to maintain muscle mass or identified whether a common "atrophy program" is activated by the various perturbations (such as denervation, starvation, unloading, immobilization, cachexia and space flight) that produce the atrophic response. Furthermore, the genetic manipulations that have been successful at maintaining muscle mass are not readily translated into therapeutic strategies.

Though the specifics are still unknown, a pattern is emerging that suggests unloading the "load-sensors" of the muscle immediately activates pro-apoptotic factors within the muscle to reduce the number of myonuclear domains (Allen et al. J Appl Physiol 1997 83:1857-1861; Allen et al. Muscle Nerve 1999 22:1350-1360). The reduction in protein synthesis then proceeds due to both reduced nuclei number (Allen et al. J Appl Physiol 1997 83: 1857-1861; Allen et al. Muscle Nerve 1999 22: 1350-1360) and reduced translation rates (Bodine et al. Nat Cell Biol 2001 3:1014-1019; Hornberger et al. Am J Physiol Cell Physiol 281: C179-187, 2001). At the same time, activation of known, and unknown, proteases begins the process of removing excess proteins from the muscle cells. Therefore, therapy against loss of functional muscle mass is believed to require targeting each of these three pathways; apoptosis, growth/protein synthesis, and protein degradation.

The Bowman-Birk inhibitor (BBI) is a well-characterized dietary protease inhibitor, with a molecular weight of approximately 8000 Da and the ability to inhibit the activity of numerous proteases, such as chymotrypsin, trypsin, cathepsin G, elastase, and chymase (Birk Y. Int J Pept Protein Res 1985 25: 113-131; Larionova et al. Biokhimiya 1993 58:1437-1444; Ware et al. Archives of Biochemistry and Biophysics 1997 344:133-138). BBI is being evaluated as an anti-carcinogenic agent in human trials in the form of a soybean extract, the Bowman-Birk Inhibitor Concentrate (BBIC) (reviewed in (Kennedy A R. Pharmacology Therapy 1998 78: 167-209). There have been no observed adverse effects following inhibition of protease activity associated with the doses of BBI evaluated in animal studies (reviewed in Kennedy A R. Pharmacology Therapy 1998 78: 167-209; Kennedy A R. Overview: Anticarcinogenic activity of protease inhibitors. In: Protease Inhibitors as Cancer Chemopreventive Agents, edited by Troll W and Kennedy A R. New York: Plenum Publishing Corp., 1993, p. 9-64). Rather, animals maintained on 1.0% dietary BBIC for their entire life had no growth abnormalities and were found to have a significantly extended life span (Kennedy et al. Nutr Cancer 1993 19:281-302). Weight loss was minimized in animals with leukemia maintained on dietary BBIC, suggesting that BBI/BBIC may reduce the muscle atrophy that occurs during cancer cachexia (Kennedy A R. Overview: Anticarcinogenic activity of protease inhibitors. In: Protease Inhibitors as Cancer Chemopreventive Agents, edited by Troll W and Kennedy A R. New York: Plenum Publishing Corp., 1993, p. 9-64). BBI has been shown to inhibit proteolytic activity in lung, kidney and liver tissue following intra-peritoneal injections in mice (Oreffo et al. Toxicology 69: 165-176, 1991). Approximately 50% of consumed BBI is able to reach the colon in an active form and is taken up into the bloodstream for distribution throughout the body (Billings et al. Cancer Lett 1992 62: 191-197; Yavelow et al. Proc Natl Acad Sci USA 1985 82: 5395-5399). Thus, BBI has been shown to be capable of entering tissues and maintaining significant inhibitory function.

It has now been found that BBI blocks the loss of functional skeletal muscle mass during periods of disuse. As shown herein, addition of Bowman-Birk Inhibitor Concentrate (BBIC) to the diet was found to significantly attenuate skeletal muscle atrophy following periods of hindlimb unloading.

The results are indicative of a composition comprising BBI or a derivative thereof providing a useful therapy to decrease skeletal muscle atrophy that arises from disuse. Further, administration of BBIC have now been found to produce functional improvement of dystrophic muscles in mdx mice, thus indicating further utility of compositions comprising BBI in treatment of degenerative muscle disorders including, but in no way limited to, muscular dystrophy, amyotrophic lateral sclerosis, spinal muscle atrophy and spinal cord injury.

The ability of a composition comprising BBI to inhibit the progression of muscle atrophy associated with disuse was demonstrated in mice by measurement of a number of physiological parameters known to change during muscle unloading. Results obtained in BBIC treated suspended and non-suspended animals were compared against those fed either aBBIC (BBIC autoclaved to remove inhibitory activity) or standard mouse feed. For each experiment, mice fed one of the three types of feed were subjected to hindlimb unloading or used as non-suspended controls.

In initial experiments, three-month-old mice were used to demonstrate the ability of BBIC-supplemented food to reduce the amount of muscle atrophy associated with hindlimb unloading. For this experiment, mice given either BBIC- or aBBIC-supplemented food were suspended for 14 days. Following suspension, the muscles were dissected and force was measured. The tetanic force was higher in the BBIC-fed animals than in the aBBIC-fed animals (130.7±22.0 mN vs. 96.9±12.4 mN, respectively (n=2 for each group). The mean specific force, measured in tension per gram muscle weight, was also higher in the BBIC-fed animals (19.2±4.0 kN/g) than in the aBBIC treated animals (16.7±2.8 kN/g). However, the muscle weight of the BBIC-fed mice (6.8±0.6 mg; n=4) was significantly greater ($p<0.05$) than the muscle weight of the aBBIC-fed mice (5.8±0.4 mg; n=4). The percent atrophy of the aBBIC-fed mice was 45.3±3.1% while the BBIC-fed mice muscle weight only declined by 33.3±2.9%.

As an increase in muscle weight was observed in the BBIC fed mice, a larger study size using six-month-old mice was performed.

In these experiments, body weights of the suspended and non-suspended mice were measured prior to and following the experimental period. The non-suspended mice in each group exhibited slight increases in body weight, ranging from ~2-5% over the 14 days. The body weight of the suspended BBIC (BBIC+HS) and aBBIC (aBBIC+HS) animals over 14 days of hindlimb suspension fell an average of 10.0±7.6% and 11.6±5.1%, respectively. The control fed suspended animals (Ctrl+HS) lost 5.0±2.3% over 14 days of suspension. This range of body mass decline has been reported previously by many studies (see refs. in Thomason, D. B. and Booth, F. W. J Appl Physiol 1990 68:1-12) and has been suggested to be due to both a reduction in total food intake and a reduction in weight gain per gram of food eaten (Morey E R. Bioscience 29: 168-172, 1979).

As the food contained the active BBI composition, food intake was measured for the animals provided the food supplemented with BBIC and aBBIC. The amount of food consumed was similar in the BBIC-fed_non-suspended (3.1±0.6 grams/day), aBBIC-fed_non-suspended (3.2±0.2 grams/day), and the aBBIC+HS (3.1±0.4 grams/day) mice. However, though not statistically significant, the BBIC+HS averaged 0.5 grams of food per day less (2.7±0.5 grams/day) than the other three groups.

To determine whether BBIC was able to attenuate muscle loss during disuse atrophy, animals fed either control food or food supplemented with BBIC were suspended for 3, 7, or 14 days. Dietary supplementation with BBIC was found to attenuate the loss of muscle mass at each time point with significant reductions in muscle loss observed following 7 days and 14 days ($p<0.05$). After 7 days hindlimb unloading, the muscle mass of the BBIC+HS animals was 8.6±0.4 mg (n=4), compared to 7.2±0.3 mg (n=4) for the Ctrl+HS animals. Following 14 days suspension, the average soleus muscle weight of the BBIC+HS animals, 7.8±0.2 mg (n=7), was significantly greater than both the aBBIC+HS (7.1±0.2 mg (n=6; $p<0.02$)) and Ctrl+HS animals (6.4±0.4 mg (n=6; $p<0.01$)). The muscle weights of the aBBIC+HS mice were greater than the Crtl+HS mice, but no significant difference was determined. The muscle weights of the non-suspended animals were the same. The muscle weights for control-fed-non-suspended, aBBIC-fed_non-suspended and BBIC-fed_non-suspended groups were 10.5±0.6 mg (n=6), 10.9±0.4 mg (n=6), and 10.6±0.5 mg (n=6) respectively. The addition of BBIC does not produce any observable hypertrophy in non-suspended muscle. The muscle weights of the Ctrl+HS and aBBIC+HS animals decreased by 39±5% and 35±3%, when compared to the control-fed_non suspended and aBBIC-fed_non-suspended mice, respectively. The percent atrophy of the BBIC+HS animals was limited to 26±4%, attenuating mass loss by 25-30% compared to the other experimental groups.

The differences in individual muscle weights relative to the body weight of the individual mice were also determined. The muscle weight was divided by the body weight of the same mouse and the result pooled and averaged for all the mice in the same group. The muscle weight to body weight ratio decreased from 0.323±0.020 mg/gram to 0.289±0.005 mg/gram for the BBIC-fed mice and from 0.341±0.038 mg/gram to 0.274±0.006 for the aBBIC fed mice. The control-fed mice muscle weight to body weight ratio declined from 0.327±0.016 mg/gram to 0.256±0.011 mg/gram. Thus, the muscle atrophy in the BBIC-fed animals (11±1%) was reduced by approximately 45-50% when compared to aBBIC-fed (20±3%) and control-fed animals (22±2%).

Average fiber number per muscle was similar for all groups suggesting that hindlimb suspension does not induce elimination of individual muscle fibers. Thus, the fiber area of the individual muscle fibers was measured in cross-sections. A simple method to determine whether there is any change in fiber size is to quantify the number of fibers in a high-powered field (40× objective). Increased fiber size reduces the number of fibers in the field of view; i.e. the smaller the muscle fibers, the greater the fiber number. Using this method, the average fiber number for the BBIC+HS animals was 61.0±5.6 (n=4) fibers per high-powered field while the aBBIC+HS group averaged 76.5±2.5 (n=4), representing a significant difference between the two groups ($p<0.05$). Both non-suspended groups were similar, averaging 40.0±1.5 (n=4) and 41.0±1.0 (n=5) for BBIC-fed_non-suspended and aBBIC-fed_non-suspended mice, respectively. Hindlimb suspension reduced the size of the muscle fibers in both BBIC and aBBIC animals as expected.

The laminin-stained muscle cross-sections were analyzed to directly measure the fiber area. The mean fiber area was significantly elevated following treatment with BBIC ($p<0.01$) when compared to the aBBIC+HS sections. The fiber area of the BBIC+HS muscles was 668±11 $\mu m^2$ (mean±SE; n=458), while the aBBIC+HS muscles decreased in fiber area to 596±10 $\mu m^2$ (mean±SE; n=353). The median fiber area was 657 $\mu m^2$ for the suspended BBIC muscles vs. 569 $\mu m^2$ for the suspended aBBIC muscles. The fiber area of the BBIC-fed_non-suspended group (957±211 $\mu m^2$; median=943 $\mu m^2$; n=71) was similar to the aBBIC-fed_non-suspended group (890±250 $\mu m^2$; median=864 $\mu m^2$; n=89).

Thus, administration of BBIC ameliorates the muscle atrophy associated with 14 days of hindlimb suspension by slowing the decrease in fiber size, thereby maintaining the overall mass of the muscle.

To determine whether the muscle remained functional, contractile measurements on the soleus muscles of both the non-suspended and suspended animals were performed in all the feed groups. The total tetanic force produced by the BBIC+HS muscles (144.1±4.3 mN; n=7) was significantly greater than the Ctrl+HS (120.9±7.9 mN; n=6), while the tension produced by the aBBIC muscles (129.7±5.4 mN; n=6) was not different (p=0.06). The force per gram muscle values are equivalent for all groups, with the Ctrl+HS, BBIC+HS, and aBBIC+HS muscles producing 18.9±1.9, 18.0±0.7, and 18.5±1.3 mN/gram muscle, respectively. The results are indicative of BBIC is maintaining functional muscle mass and enabling overall greater force production by the muscle.

Changes in muscle mass observed in the mice where correlated with BBIC intake. More specifically, the quantity of food consumed over the 14-day experimental period was plotted against the muscle weights of the individual mice. The results were indicative of a positive correlation between the amount of BBIC food consumed per day and the muscle weight. The effect of BBIC on the muscle weights as a function of food intake per day were calculated to be significantly different from zero (p<0.05), while no significant effect of aBBIC intake was determined (p=0.7). Re-evaluation of the BBIC-fed animals to the subset that consumed >3.0 grams/day of feed showed a further reduction in the amount of muscle atrophy with the soleus muscle mass averaging 8.2±0.2 mg (n=3). Similar analysis in the aBBIC fed mice indicated no such change with the soleus muscle mass averaging 7.2±0.2 mg (n=4). Further, there was no significant difference (p=0.4) in the muscle-to-body weight ratio between the BBIC-fed_non-suspended and BBIC+HS animals consuming greater than 3.0 grams per day. This indicates increased consumption of BBIC reduced the degree of muscle atrophy to insignificant levels. While the absolute muscle weights were still significantly lower in the BBIC+HS animals than the BBIC-fed_non-suspended mice, the percent atrophy, in terms of the muscle to body weight ratio, was reduced from 19.4±1.8% in the aBBIC-fed mice to 7.2±0.6% (n=3) in the BBIC-fed mice. These results indicated that the quantity of food, or more specifically the quantity of BBIC, consumed is important in reducing the amount of muscle atrophy associated with hindlimb unloading.

In additional experiments, osmotic pumps were inserted to directly deliver either BBIC or aBBIC to six month old mice. Each animal had an Alzet osmotic pump (Alza, Palo Alto, Calif.) containing either BBIC (10% w/v) or autoclaved BBIC (10% w/v) surgically inserted on the anterior portion of the back, directly under the skin. The pumps release the solution constantly over a period of two weeks at a rate of 0.5 μl/hr. Again, the muscle weights of the BBIC treated mice (8.1±0.1 mg, 22% atrophy; n=4), were greater than the muscle weights of the aBBIC muscle weights (7.4±0.7 mg, 31% atrophy; n=4), although the difference observed between the treatment groups was not statistically significant. The maintenance of muscle mass by BBIC again resulted in approximately 30% enhancement in muscle weight following 14 days suspension. Experiments were also performed in mdx mice, a murine model for Duchenne muscular dystrophy.

In these experiments, treatment of male mdx mice with a composition comprising BBI, specifically food supplemented with 1.0% BBIC, was initiated at four weeks of age and continued for 12 weeks. The weights of the animals were monitored and recorded each week. No difference in body weight increases between the control mdx mice and those provided food supplemented with 1.0% BBIC were observed. In addition, as a further control, wild type C57BL/6 mice were provided food supplemented with 1% BBIC to determine whether BBIC induced any changes in normal, non-dystrophic muscle size or function. Following six weeks of feeding with 1.0% BBIC, there were no changes in either muscle mass or strength when compared with the animals in the wild type C57BL/6 mice not receiving the BBIC supplemented diet.

The diaphragm of mdx mice exhibits considerable fibrosis at 4 months of age that is observable using routine hematoxylin-eosin (H&E) staining. Greater differentiation of fibrotic tissue from the muscle cells can be achieved using trichrome method which stains muscle tissue red and stains fibrotic and connective tissue dark blue. Feeding with 1.0% BBIC was found to markedly improve the appearance of the diaphragms of mdx mice stained using H&E and trichrome as compared to control mdx mice.

Further, the muscle fibers of the mdx mouse undergo pronounced cycles of degeneration/regeneration beginning at approximately 4 weeks of age. Regeneration of muscle fibers requires activation and fusion of satellite cells that appear in the center of the regenerating fibers. Thus, a measure of regenerating muscle fibers is the presence of central nucleated muscle fibers (CNF) with an increased proportion of CNFs representing increased regeneration. Muscle sections were stained with laminin to outline the muscle fibers and the nuclei were stained with the nuclear stain 4,6-diamidino-2-phenylindole. For each muscle, the number of CNFs was determined as a proportion of the total fiber number with a total of 2-4 muscles used for each measurement. A significant reduction in the proportion of CNFs in the tibialis anterior muscles was observed following BBIC treatment (p<0.05, n=3 for control, n=4 for BBIC-fed). Non-significant reductions in the BBIC-treated mice were observed in the EDL and diaphragm muscles (p=0.064 and p=0.058, respectively). However, as a larger sample size for the tibialis anterior produced significant results, it is anticipated that similarly increasing the number of animals will produce a significant difference in both the EDL and diaphragm muscles (presently, n=2).

Evan's blue dye was used to determine the membrane integrity of both untreated and BBIC-treated mdx mice. Twenty-four hours prior to sacrifice, the animals were intraperitoneal injected with Evan's Blue dye. The muscles were sectioned, fixed and observed under a fluorescent microscope to determine the degree of membrane damage. Increased regions of infiltration were observed in the quadricep muscles of an untreated mdx animal. The diaphragm muscles of both groups appeared to have limited EBD uptake.

When compared to non-dystrophic animals, the EDL muscles of mdx mice have increased mass and cross-sectional area. However, the increase in mass does not correlate to an improvement in the force per cross-sectional area (specific force), rather there is a significant decline in the specific force of mdx muscles. Supplementation with 1.0% BBIC significantly increased muscle mass, absolute force, and cross-sectional area, while maintaining specific force (p<0.05; n>5 for each measurement). These results indicate strength improvement is gained via BBIC feeding. Though the specific force is unchanged, the increased muscle mass and absolute force provides the animal with a greater ability to perform everyday tasks. The increased muscle mass is not simply due to an overall increase in body weight as there is a significant increase in the muscle weight to body weight ratio.

Thus, as demonstrated by each of the above-described tests, there were significant improvements in multiple morphological and functional measurements of skeletal muscle following twelve weeks of BBIC consumption by mice of this murine model for Duchenne muscular dystrophy.

Accordingly, the present invention provides methods for use of a composition comprising Bowman-Birk Inhibitor (BBI) or a derivative thereof in the treatment and/or prevention of skeletal muscle atrophy. In one embodiment of this method, the composition administered comprises Bowman Birk Inhibitor Concentrate. While various routes of administration have been demonstrated to be effective for compositions comprising BBI or a derivative thereof, oral may be most desirable as it is least invasive to a subject receiving treatment. For example, the ability to prevent functional muscle loss via simple dietary supplementation with a composition comprising BBI or a derivative thereof is expected to lead to improvement in quality of life for the aging population, speed recovery from prolonged bed rest or limb immobilization (casting), and may even provide astronauts with a greater ability to endure space travel.

As also demonstrated herein, administration of a composition comprising BBI improved skeletal muscle function, as determined by both increased strength and increased mass of the muscle, in a murine model for a degenerative skeletal muscle disorder. Thus, the present invention also provides methods for use of a composition comprising Bowman-Birk Inhibitor (BBI) or a derivative thereof to improve skeletal muscle function. In one embodiment of this method, the composition administered comprises Bowman Birk Inhibitor Concentrate. While various routes of administration have been demonstrated to be effective for compositions comprising BBI or a derivative thereof, oral may be most desirable as it is least invasive to a subject receiving treatment.

Further, the present invention provides methods for alleviating symptoms and/or slowing of progression of degenerative skeletal muscle diseases or disorders. As demonstrated herein, treatment with a composition comprising BBI produced significant improvement in skeletal muscle function in a murine model for the degenerative skeletal muscle disorder, Duchenne muscular dystrophy. These results are indicative of treatment with a composition comprising BBI or a derivative thereof being useful in alleviating symptoms or slowing progression of any degenerative skeletal muscle disorder wherein degeneration of the muscle relates to changes in protein synthesis and/or protein degradation. In one embodiment of this method, the composition administered comprises Bowman Birk Inhibitor Concentrate. While various routes of administration have been demonstrated to be effective for compositions comprising BBI or a derivative thereof, oral may be most desirable as it is least invasive to a subject receiving treatment.

For purposes of the present invention, by "alleviating symptoms" it is meant that any myalgia, myositis, myotonia and/or loss in muscle strength associated with degeneration of the skeletal muscle is lessened by treatment with a composition comprising BBI or a derivative thereof.

By the phrase "slowing of progression" it is meant that muscle wasting and/or loss in muscle strength associated with degeneration of the skeletal muscle occurs less rapidly upon treatment with a composition comprising BBI or a derivative thereof.

By "BBI or derivative thereof" it is meant to include any Bowman Birk Inhibitor or Bowman Birk Inhibitor product, including, but not limited to, BBI prepared by methods known in the art, BBI concentrates prepared in accordance with methods known in the art including, but not limited to those taught in U.S. Pat. No. 5,217,717 (which is incorporated herein by reference in its entirety), and any synthetically derived compounds which mimic the biological activities, and in particular the serine protease inhibitory activity, of BBI. By "synthetic" it is meant to include both recombinant and chemical means for compound production. Compositions comprising BBI or a derivative thereof are administered in an effective amount, either as a prophylactic dietary supplement or a pharmaceutical. The term "effective amount" refers to an amount which prevents skeletal muscle atrophy and/or improves skeletal muscle function as determined by increased strength and/or muscle mass, and/or alleviates symptoms or slows progression of a degenerative muscle disorder. Such an amount can be determined by those of skill in the art in accordance with known methods.

Compositions of the present invention may be administered parenterally, rectally, topically, transdermally or orally, preferably orally. Examples of pharmaceutical or prophylactic dietary supplement formulations include, but are not limited to, syrups, suspensions, emulsions, tablets, capsules, lozenges and mouthwashes.

In one embodiment of the invention, the composition is administered as a liquid formulation comprising a suspension or solution of the composition in a pharmaceutically acceptable liquid carrier. Suitable liquid carriers include, but are not limited to, ethanol, glycerin, non-aqueous solvents such as polyethylene glycols, oils or water with a suspending agent, preservatives, flavorings or coloring agents, or any suitable combination thereof.

Another liquid formulation of a composition comprising BBI or a derivative thereof useful in the present invention is a stable mouthwash solution that provides extended mucosal contact time, is palatable, easy to administer and suitable for low cost mass production. A saliva substitute provides the solution with the necessary viscosity to increase mucosal contact time and bioavailability, and has been shown to provide sustained release of many compounds. In one formulation, BBI Concentrate (BBIC) product, a saliva substitute such as sorbitol, carboxymethylcellulose, or methylparaben and water are included.

In another embodiment, a composition in the form of a tablet is prepared using any suitable pharmaceutical carrier routinely used for preparing solid formulations. Examples of such carriers include, but are not limited to, magnesium stearate, starch, lactose, sucrose and cellulose.

Compositions in the form of capsules can also be prepared using routine encapsulating procedure. For example, pellets, granules or powder containing a composition comprising BBI or a derivative thereof can be prepared using standard carriers and then filled into a hard gelatin capsule. Alternatively, a dispersion or suspension can be prepared using any suitable pharmaceutical carrier(s) and the dispersion or suspension is then filled into a soft gelatin capsule. Suitable pharmaceutical carriers include, but are not limited to, aqueous gums, cellulose, silicates and oils.

In yet another embodiment, a composition for parenteral administration is formulated as a solution or suspension. This solution or suspension will generally include the composition of the instant invention in a sterile aqueous carrier or parenterally acceptable oil. Examples of parenterally acceptable oils include, but are not limited to, polyethylene glycol, polyvinyl pyrrolidone, lecithin, arachis oils and sesame oil. Alternatively, the solution can be lyophilized and then reconstituted with a suitable solvent just prior to administration to a subject.

By "subject", as used herein it is meant to include, but is not limited to, any mammal including humans.

The following nonlimiting examples are provided to further illustrate the present invention.

EXAMPLES

Example 1

Preparation of Bowman-Birk Inhibitor Concentrate (BBIC)

BBIC was purified in accordance with procedures described by Kennedy et al. (Nutr Cancer 1993 19: 281-302) and Yavelow et al. Proc Natl Acad Sci USA 1985 82: 5395-5399). This purification procedure maintains the chymotrypsin inhibitor activity but reduces the level of trypsin inhibitory activity, as high levels of trypsin inhibitory activity have been shown to cause a potentially deleterious pancreatic feedback response in rats (Kennedy et al. Nutr Cancer 1993 19: 281-302; Kennedy, A. R. Pharmacology Therapy 1998 78: 167-209). BBIC was prepared by Central Soya Co. Inc. (Ft. Wayne, Ind.). The purified BBIC was then used to produce pellets of mouse food for oral consumption. The diet used was Rodent Diet AIN-93G (Bio-Serv, Frenchtown, N.J.) with dietary supplements of 1.0% BBIC or 1.0% autoclaved BBIC (aBBIC) in which the protease inhibitor activity has been destroyed by autoclaving. The animal group receiving 1.0% aBBIC, with no chymotrypsin inhibitor activity, represents an isocaloric diet control for the group receiving 1.0% BBIC. The standard mouse food, as well as food supplemented with BBIC and aBBIC was provided ad libitum. The observed physiological changes of the BBIC-fed mice were compared to those receiving either the standard mouse food or food supplemented with aBBIC.

Example 2

Animals

The experiments in this study were approved by the University of Pennsylvania's Institutional Animal Care and Use Committee. Three and six-month-old male C57/B16 mice were used for this study and were randomly assigned to one of the experimental groups. More specifically, animals were randomly separated into one of three feed groups; BBIC, aBBIC or control. The animals were switched to the experimental diets, containing 1.0% BBIC, 1.0% aBBIC or no additional supplementation 5-7 days prior to the beginning of the experimental period. From each of the three feed groups, half were placed in individual cages to be used as non-suspended controls, while the others were hindlimb suspended in individual suspension cages. Thus, the animals were randomly assigned to one of six groups: 1.) Control, non-suspended; 2.) Control, hindlimb suspended (Ctrl+HS); 3.) BBIC-fed_non-suspended; 4.) BBIC, hindlimb suspended (BBIC+HS); 5.) aBBIC-fed_non-suspended; and 6.) aBBIC, hindlimb suspended (aBBIC+HS).

Example 3

Hindlimb Suspension

The animals were suspended using a modified tail suspension technique originally described for rats by Morey, E. R. (Bioscience 1979 29: 168-172) and adapted herein for mice. In these experiments, the animals were anesthetized using a mixture of ketamine and xylazine and the body weight measured. The tails were cleaned and attached to a stainless steel chain using a strip of adhesive tape (Skin Trac (Zimmer, Warsaw Ind.)). The animals were suspended by attaching the chain to a support running on a track at the top of the cage that enabled the mice to move freely around the cage while preventing the hindlimbs from touching the floor or walls.

Example 4

Muscle Mechanical Measurements

Following a 3-, 7- or 14-day suspension period both the suspended and non-suspended control mice were anesthetized, the body weight measured and the soleus and gastrocnemius muscles removed. One soleus muscle was dissected and prepared for mechanical muscle force measurements in accordance with procedures described by Barton-Davis et al. *Proc Natl Acad Sci USA* 1998 95: 15603-15607). The resting length (Lo) was set by adjusting muscle length until maximal twitch tension was obtained. Maximal tetanic force was measured by stimulating the soleus muscles with a 100 Hz, 500 ms pulse at supramaximal voltage. Following the tension measurements, the muscle was blotted, weighed and then rapidly frozen in melting isopentane and stored at −80° C. for subsequent histological analysis. The other soleus muscle to be used for biochemical analysis, without any ex vivo stimulation, was weighed and immediately frozen and stored in liquid nitrogen. The gastrocnemius muscles were also frozen for biochemical analyses.

Example 5

Statistical Analysis

Statistical significance was determined by applying the raw data to either an unpaired t test or a one-way ANOVA where applicable. The data are shown as mean±SEM unless otherwise noted.

Example 6

Fiber Size Determination

Frozen sections (10 µm) were washed in PBS and blocked in 5% BSA in PBS for 1 hour. The sections were then incubated in 5% BSA/PBS containing a primary antibody against laminin (NeoMarkers, Fremont, Calif.) at a 1:250 dilution. A rhodamine-conjugated anti-rabbit IgG was used as a secondary antibody (Jackson Immunoresearch Laboratories) to visualize staining. The slides were mounted with Vectashield (Vector Labs, Burlingame Vt.) to slow photobleaching. Microscopy was performed on a Leitz DMR microscope (Leica) and image acquisition and analysis was performed using a MicroMAX digital camera system (Princeton Instruments, Inc.) and imaging software (OpenLab, Signal Analytics).

Example 7

Experiments in mdx Mice

Four week old male mdx mice were randomly assigned to either a control group, supplied food with no added BBIC, or BBIC-fed group, supplied with food supplemented with 1% BBIC. All food was provided ad libitum. Following the 12-week experimental feeding period the mice were anesthetized, the body weight measured and the muscles removed. One extensor digitalis muscle was dissected and prepared for mechanical muscle force measurements, as described supra in Example 4. The resting length (Lo) was set by adjusting muscle length until obtaining maximal twitch tension. Maximal tetanic force was measured by stimulating the muscles with a 120 Hz, 500 ms pulse at supramaximal voltage. Following the tension measurements, the muscle was blotted, weighed and then rapidly frozen in melting isopentane and stored at −80° C. for subsequent histological analysis. The other muscles were weighed and frozen immediately for either histological or biochemical analysis.

For each animal the extensor digitalis longus, diaphragm, gastrocnemius, and quadriceps muscles were sectioned in a cryostat and slides were prepared for standard histological assessment using hematoxylin-eosin and trichrome staining. Several animals from both the control and BBIC groups were injected with Evan's Blue dye to observe possible changes in membrane integrity. In particular, the night prior to sacrifice, the mice were injected with 0.2 ml of 0.2% Evan's blue dye in PBS. Membrane damage was assessed by visualization of Evan's blue fluorescence in fibers of the diaphragm and quadriceps muscles.

Microscopy was performed on a Leitz DMR microscope (Leica) and image acquisition and analysis was completed using a MicroMAX digital camera system (Princeton Instruments, Inc.) and imaging software (OpenLab, Improvision Inc. Waltham, Mass.).

What is claimed is:

1. A method for slowing progression of skeletal muscle atrophy in a subject comprising administering to the subject a composition comprising a therapeutically effective amount of Bowman-Birk Inhibitor.

2. The method of claim 1 wherein the composition is administered orally.

3. The method of claim 2 wherein the composition is administered as a dietary supplement.

4. The method of claim 1 wherein the Bowman-Birk Inhibitor is in a concentrated form.

5. A method for improving skeletal muscle function in a subject in need thereof comprising administering to the subject a composition comprising a therapeutically effective amount of Bowman-Birk Inhibitor wherein improved skeletal muscle function comprises increased muscle strength or increased muscle mass.

6. The method of claim 5 wherein the composition is administered orally.

7. The method of claim 6 wherein the composition is administered as a dietary supplement.

8. The method of claim 5 wherein the Bowman-Birk Inhibitor is in a concentrated form.

9. A method for treating skeletal muscle degeneration in a subject comprising administering to the subject a composition comprising a therapeutically effective amount of Bowman-Birk Inhibitor.

10. The method of claim 9 wherein the composition is administered orally.

11. The method of claim 10 wherein the Bowman-Birk Inhibitor is in a concentrated form.

12. The method of claim 9 wherein the composition comprises Bowman-Birk Inhibitor Concentrate.

13. A method for slowing progression of a degenerative skeletal muscle disorder or disease in a subject in need thereof comprising administering to the subject a composition comprising a therapeutically effective amount of Bowman-Birk Inhibitor.

14. The method of claim 13 wherein the composition is administered orally.

15. The method of claim 14 wherein the composition is administered as a dietary supplement.

16. The method of claim 13 wherein the Bowman-Birk Inhibitor is in a concentrated form.

17. The method of claim 13 wherein the degenerative skeletal muscle disorder or disease is muscular dystrophy, amyotrophic lateral sclerosis, spinal muscle atrophy or spinal cord injury.

* * * * *